(12) United States Patent
Cagle

(10) Patent No.: US 10,751,295 B2
(45) Date of Patent: Aug. 25, 2020

(54) COMPOSITIONS AND METHODS FOR THE REMOVAL OF EAR WAX

(71) Applicant: Specialty Drug and Device, LLC, Fort Worth, TX (US)

(72) Inventor: Chris Cagle, Fort Worth, TX (US)

(73) Assignee: Specialty Drug and Device, LLC, Fort Worth, TX (US)

( * ) Notice: Subject to any disclaimer, the term of this patent is extended or adjusted under 35 U.S.C. 154(b) by 0 days.

(21) Appl. No.: 15/591,857

(22) Filed: May 10, 2017

(65) Prior Publication Data

US 2018/0125793 A1    May 10, 2018

Related U.S. Application Data

(60) Provisional application No. 62/419,777, filed on Nov. 9, 2016.

(51) Int. Cl.
| | | |
|---|---|---|
| *A61K 31/02* | (2006.01) | |
| *A61J 1/06* | (2006.01) | |
| *B32B 1/00* | (2006.01) | |
| *A61J 1/16* | (2006.01) | |
| *A61J 1/14* | (2006.01) | |
| *A61K 9/00* | (2006.01) | |
| *A61K 9/107* | (2006.01) | |
| *A61K 47/02* | (2006.01) | |
| *A61K 47/10* | (2017.01) | |
| *A61K 47/12* | (2006.01) | |
| *A61K 47/26* | (2006.01) | |
| *A61M 11/00* | (2006.01) | |
| *B65B 3/00* | (2006.01) | |
| *B65B 7/28* | (2006.01) | |
| *A61J 7/00* | (2006.01) | |

(52) U.S. Cl.
CPC ............ *A61K 31/02* (2013.01); *A61J 1/06* (2013.01); *A61J 1/1412* (2013.01); *A61J 1/16* (2013.01); *A61K 9/0046* (2013.01); *A61K 9/107* (2013.01); *A61K 47/02* (2013.01); *A61K 47/10* (2013.01); *A61K 47/12* (2013.01); *A61K 47/26* (2013.01); *A61M 11/00* (2013.01); *B32B 1/00* (2013.01); *B65B 3/003* (2013.01); *B65B 7/28* (2013.01); *A61J 7/003* (2013.01); *A61J 7/0053* (2013.01); *A61M 2210/0662* (2013.01)

(58) Field of Classification Search
CPC ............... A61K 9/0046; B65B 3/003; A61M 2210/0662; A61M 11/00
See application file for complete search history.

(56) References Cited

U.S. PATENT DOCUMENTS

| | | | |
|---|---|---|---|
| 4,895,875 A | 1/1990 | Winston | |
| 5,296,472 A | 3/1994 | Sanchez et al. | |
| 5,480,658 A | 1/1996 | Melman | |
| 2004/0126436 A1* | 7/2004 | Cagle | A61K 9/0046 424/717 |
| 2014/0348959 A1* | 11/2014 | Mitchnick | A61K 36/235 424/725 |

FOREIGN PATENT DOCUMENTS

| | | |
|---|---|---|
| CN | 1994317 A | 7/2007 |
| EP | 2708228 A1 | 3/2014 |
| WO | 2003003976 A2 | 1/2003 |
| WO | 2012052418 A1 | 4/2012 |
| WO | 2012160179 | * 11/2012 |
| WO | 2012160179 A2 | 11/2012 |
| WO | 2014041055 A1 | 3/2014 |

OTHER PUBLICATIONS

Ashley Marcin, Tips for Cleaning Your Ears Safely; Healthline; published Jul. 5, 2016. Downloaded from https://www.healthline.com/health/how-to-clean-your-ears. (Year: 2016).*
Calvert, title: Bubbles and soaps, Mar. 20, 2004. (Year: 2004).*
Unknow author names, title: Why do we think cleaning agents must have bubbles? Straight Dope Message Board, Jun. 3, 2004 (Year: 2004).*
International Search Report and Written Opinion by the Australian Patent Office for PCT/US2017/060625, dated Dec. 19, 2017, 13 pp.

* cited by examiner

*Primary Examiner* — Yanzhi Zhang
(74) *Attorney, Agent, or Firm* — Edwin S. Flores; Chalker Flores, LLP

(57) ABSTRACT

The present invention includes compositions and methods for the treatment, softening and removal of ear wax by administering to the ear a solution of a semi-fluorinated alkane according to the formula: RFRH or RFRHRF, wherein RF is a perfluorinated hydrocarbon segment with 20 or less carbon atoms, and RH is a non-fluorinated hydrocarbon segment with 3 to 20 carbon atoms.

25 Claims, No Drawings

COMPOSITIONS AND METHODS FOR THE REMOVAL OF EAR WAX

CROSS-REFERENCE TO RELATED APPLICATIONS

This application claims priority to U.S. Provisional Application Ser. No. 62/419,777, filed Nov. 9, 2016, the entire contents of which are incorporated herein by reference.

STATEMENT OF FEDERALLY FUNDED RESEARCH

None.

TECHNICAL FIELD OF THE INVENTION

The invention generally pertains to the removal of ear wax (cerumen) from the ears of both animals and humans and to preventing accumulation of cerumen in the ear canal. More particularly, but not by way of limitation, the present invention is directed to advantageous compositions and methods of ear wax removal.

BACKGROUND OF THE INVENTION

Without limiting the scope of the invention, its background is described in connection with ear wax removal.

Cerumen (ear wax) is a slightly yellow waxy substance that is found in the ear canal of humans and other mammals. Ear wax is composed of a variety of waxes secreted by ceruminous glands located in the ear canal; sebum from oil glands, desquamated epithelial cells, along with other materials. Together, these materials combine to form a greasy wax that helps protect the passageway into the ear. Cerumen also acts as a demulcent, forming a protective layer over the skin of the external ear canal. The composition, as well as physical characteristics of ear wax, including quantity, consistency and color of ear wax varies among individuals. These factors, along with genetic factors and regular ear hygiene contribute to accumulation of ear wax and difficulties that can be encountered when trying to remove it.

Accumulation and impaction of ear wax in the external ear canal is a significant problem. Cerumen impaction occurs more frequently in older populations, among people who wear hearing aids and ear plugs and is associated with overuse of cotton buds used to swab the ear canal, as well as in individuals with congenital deformities of the ear canal. Individuals possessing hairy ear canals are also disposed to ear wax build-up. Additionally, ear wax accumulation can also be a problem in infants. Individuals who experience accumulation or impaction of ear wax may suffer ear pain, difficulty in hearing, tinnitus, irritation and itching. It is usually necessary to remove ear wax to alleviate these conditions. Physician office visits are common, necessary and can be costly for the purpose of removing excess or impacted cerumen from patients' ears.

Over-the-counter (OTC) wax softening products often contain carbamide peroxide as an active ingredient (FDA monograph part 344.). Debrox Drops Earwax Removal Aid, available from Smith Kline Beecham of Pittsburgh, Pa. is one such product; another is Murine Ear drops manufactured by Abbott Laboratories, Columbus, Ohio, Flents Earwax Remover is produced by Flents Products Co of Yonkers, N.Y. These monographed products contain 6.5% carbamide peroxide in a glycerin vehicle. To use these products, drops are placed in the affected ear, the individual waits a few minutes and then tilts his/her head to the side to allow drainage of excess liquid. In addition to OTC earwax remedies, a prescription product, Cerumenex Eardrops, is also available. The product contains triethanolamine polypeptide oleate-condensate (10%), as an active ingredient, and is available from the Purdue Frederick Company of Norwalk, Conn. Triethanolamine polypeptide oleate-condensate is a surfactant that helps emulsify ear wax; an application of the product requires about 30 minutes. Cerumenex sometimes results in irritation of the ear canal, a type of localized dermatitis.

In addition to the foregoing, other preparations have been used to soften and help remove ear wax. These agents include sodium bicarbonate, hydrogen peroxide, glycerin and oils, such as olive oil, mineral oil, etc. Most commonly, when one of these remedies is used, irrigation with warm water or saline solution is employed to help remove cerumen.

Hydrogen peroxides can sometimes cause irritation of the ear canal. U.S. patents have covered some of these kinds of products. For instance, U.S. Pat. No. 5,296,472 (Sanchez et al) describes oil-free cyclodextrin compositions that are useful for cerumen removal; U.S. Pat. No. 4,895,875 (Winston) discloses compositions containing stabilized hydrogen peroxide, urea, and glycerin that have utility for the removal of ear wax; and U.S. Pat. No. 5,480,658 (Melman) discloses compositions comprising acetic acid and boric acid in a water base useful for cleaning the external ear canal of pets.

Aqueous solutions of percent sodium bicarbonate (5%) have also been used by physicians to remove accumulated ear wax. Glycerin may also be added because of its abilities to soften cerumen and its demulcent activity. Because products containing sodium bicarbonate are not stable, products of this type must be compounded relatively frequently and to date have not been commercialized.

Several home remedies, OTC products, and a surfactant-containing prescription are available and used for removal of cerumen. Nonetheless, a clear-cut need remains for improved compositions that will remove ear wax from animals and humans in a relatively short period of time and do so safely. Products that have the ability to soften or dissolve impacted ear wax and also quickly, and can be used to help prevent accumulation of ear wax will also be of significant benefit.

Liquid semifluorinated alkanes (SFAs) have been used commercially for medical purposes for about two decades. SFAs are used in the eye to replace vitreous humor, the material located posterior to the crystalline lens; as a tamponade in retinal detachment and as an adjunct to unfolding and holding in place a detached retina (Meinert, H. et al., Europ J Ophthalmol. 10(3), p 583-595. 1993). Such application has shown SFAs to be well-tolerated, even in sensitive and delicate organs such as the inside of the eye.

SUMMARY OF THE INVENTION

The present invention provides for novel compositions and methods for administration to the ear of a semi-fluorinated alkane (SFA) according to the formula RFRH or RFRHRF, wherein RF is a perfluorinated hydrocarbon segment with 20 or less carbon atoms, and RH is a non-fluorinated hydrocarbon segment with 3 to 20 carbon atoms in an amount sufficient to at least partially or completely remove cerumen. In a preferred embodiment, the SFA is selected from F4H5, F4H6, F4H8, F6H6 and F6H8. In one aspect, the semifluorinated alkane is a compound of formula: RFRH, wherein RF is a linear perfluorinated hydrocarbon segment with 4 to 12 carbon atoms, and wherein RH is a linear alkyl group with 4 to 8 carbon atoms. In another aspect, the semifluorinated alkane is selected from at least one of F4H5, F4H6, F4H8, F6H6 and F6H8. In another aspect, the composition is in the form of a solution, spray or suspension, emulsions, or microemulsions. In another aspect, the composition comprises a cosolvent that is physiologically compatible, selected from glycerol, propylene glycol, polyethylene glycol, triglyceride oils, liquid mono or diglycerides and hydrofluorocarbons. In another aspect, the composition further comprises a surfactant selected from at least one of polysorbates, 4-(1,1,3,3-tetramethylbutyl) phenol/poly(oxyethylene) polymers, poly(oxyethylene-poly (oxypropylene) block copolymers, polyethylene glycol esters of fatty acids, or polyoxypropylene ethers of higher alkanes (C12-C18). In another aspect, the composition further comprises a compound selected from at least one of: sodium carbonate, sodium bicarbonate, or sodium perborate. In another aspect, the composition further comprises a demulcent that is glycerin or mineral oil. In another aspect, the composition further comprises a demulcent present in the amount of about 1 weight/volume percent to about 20 weight/volume percent. In another aspect, the composition further comprises a preservative selected from at least one of: benzalkonium chloride or other quarternary ammonium preservative, stabilized oxychloro complexes (Purite), sodium perborate, or mixtures thereof. In another aspect, the composition is packaged in an acceptable container coated internally with materials to prevent vapor permeation of the SFA through the packaging material or the package is overwrapped with polymer to prevent escape of the SFA. In another aspect, the composition is packaged in a plastic container. In another aspect, the composition is inserted in a package fitted with a cap-sprayer of a diameter from 0.2 cm to 0.4 cm such that it is capable of being inserted into the ear canal, and the cap-sprayer is cap is from 1.9 cm to 2.4 cm in length. In another aspect, the composition is inserted in a package fitted with a cap-sprayer with an extension for fitting into the ear canal. In another aspect, the composition is in cotton buds wetted with that composition. In another aspect, the composition is in cotton buds wetted with that composition in individually sealed in an acceptable unit-of-use packaging material, wherein the packaging material is capable of preventing diffusion of the composition from the package. In another aspect, the composition is adapted for administration to an animal. In another aspect, the composition is an emulsion comprising about 40 wt-% SFA to 60 wt-% water, to SFA and 60 wt-% to 40 wt-% water. In another aspect, the composition is an emulsion with a particle size of at least 5 nm and less than 200 nm. In another aspect, the composition is a microemulsion in a liquid composed of 20 to 95 wt-% SFA.

In another embodiment, the present invention includes a composition for the treatment, softening and removal of ear wax by administering to the ear a solution of a semifluorinated alkane (SFA) according to the formula: RFRH or RFRHRF, wherein RF is a perfluorinated hydrocarbon segment with 20 or less carbon atoms, and RH is a non-fluorinated hydrocarbon segment with 3 to 20 carbon atoms, and the composition is adapted for administration to the ear canal. In one aspect, the semifluorinated alkane is selected from F4H5, F4H6, F4H8, F6H6 and F6H8. In another aspect, the composition is in the form of a solution, spray or suspension, emulsions, or microemulsions. In another aspect, the composition further comprises a cosolvent that is physiologically compatible, selected from glycerol, propylene glycol, polyethylene glycol, triglyceride oils, liquid mono or diglycerides and hydrofluorocarbons. In another aspect, the composition further comprises a surfactant selected from at least one of polysorbates, 4-(1,1,3,3-tetramethylbutyl) phenol/poly(oxyethylene) polymers, poly(oxyethylene-poly(oxypropylene) block copolymers, polyethylene glycol esters of fatty acids, or polyoxypropylene ethers of higher alkanes ($C_{12}$-$C_{18}$). In another aspect, the composition is an emulsion comprising about 40 wt-% SFA to 60 wt-% water, to SFA and 60 wt-% to 40 wt-% water. In another aspect, the composition is an emulsion with a particle size of at least 5 nm and less than 200 nm. In another aspect, the composition is a microemulsion in a liquid composed of 20 to 95 wt-% SFA.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and does not limit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

It has been surprisingly found by the inventors that certain SFAs are capable of dissolving cerumen from both animals and humans. In these studies, which are reflected below in Table 1, samples of ear wax were collected on cotton buds from animals or humans. A portion of each sample was placed into a small tube containing an SFA (F6H8) and gently shaken. In seconds, the cerumen from the ear wax sample dissolved completely.

The composition may, however, be in the form of a solution, gel, emulsion, suspension or spray. The agent is useful for administering a broad range of agents that also have utility in the softening, dissolution and removal of ear wax, including glycerol, propylene glycol, polyethylene glycol, pentylene glycol, liquid paraffin, triglyceride oils, hydrofluorocarbons, liquid mono- or diglycerides and sodium perborate.

Compositions may include SFAs; bicarbonate and/or glycerin. The composition may contain a suitable preservative, for example, benzalkonium chloride or other quarternary ammonium preservatives, including polyquarternium 1 (POLYQUAD®); polyhexanides such as polyhexamethylene biguanide (PHMB); a stabilized oxychloro complex (Purite); or sodium perborate. Other preservatives may also be used as long as they are compatible with the SFAs.

Liquid SFAs are molecules that are chemically and physiologically inert, colorless and stable. The density of SFAs range from 1.1 to 1.7 g/cm$^3$ and have low surface tensions, down to 19 mN/m. Many SFAs are not miscible with water, though some members of the class, as well as other structurally related molecules, may be more amphiphilic. Generally speaking, the lipophilicity of SFAs increases directly with the length of the non-fluorinated segment of the molecule. Preferred compositions for the removal of ear wax from animal or human ears utilize a SFA with a density >1.15 g/cm$^3$.

The invention provides for novel approaches of applying SFA compositions with or without the addition of other co-solvents; with or without the addition of demulcents; with or without addition of demulcents; with or without the addition of a bicarbonate and with or without the addition of an antimicrobial preservative. Compositions are intended to be applied to the ear for the removal of cerumen by a pump-actuated spray or to clean and remove small amounts of ear wax with the use of cotton buds wetted with composition. Compositions each include a SFA whose structure may be represented by RFRH or RFRHRF where RF is a perfluorinated hydrocarbon segment of less than 20 carbon atoms and RH is a non-fluorinated hydrocarbon chain with 3 to 20 carbon atoms. Preferred embodiments of the SFA used in compositions include, e.g., F4H5, F4H6, F4H8, F6H6, and F6H8.

Compositions may also be composed of more than one SFA. For instance, it maybe be desirable to combine SFAs in order to achieve certain physical/chemical characteristics of the formulation or to achieve enhance solubilization of the cerumen or formulate a composition viscosity that is matched to desired spray characteristics from a suitable container. In such cases, it is anticipated the mixture will contain one of the following SFAs: F4H5, F4H6, F4H8, F6H6, and F6H8.

The invention is based in substantial part upon initial studies that provided surprising results. A small quantity of F6H8 semi-fluorinated alkane was placed into each of 5 test tubes. Samples of cerumen from animal or human ears were collected on cotton buds. Sufficient ear wax was collected that quantities of the material were visible on cotton buds used to harvest the materials. Separate cotton buds were used to collect cerumen from four dogs and two humans. In a step-wise manner, one cotton bud, laden with ear wax, was gently swirled through a single test tube containing an aliquot of F6H8 SFA. The study was repeated three times for cotton buds with ear wax from dogs and a second series of two tests, as previously described, were carried-out with cotton buds laden with human cerumen. In each case, the cerumen from the ear wax sample dissolved completely in the SFA. Importantly, in the study the cerumen was dissolved by the SFA but the other matter (hair particles, etc.) were not dissolved. These results were unanticipated considering the inability of commercial products to easily dissolve ear wax and the time called-out in product instructions of 5 minutes to as long as 30 minutes. Such products include MURINE® Ear Drops, DEBROX® Earwax Removal, Flents Earwax Remover, and CERUMENEX® and also includes patents for compositions containing glycerin, glycols, peroxide plus urea and cyclodextrin containing compositions.

Compositions claimed herein are safe for topical application and are to be employed in the form of a solution, spray or suspension, terms that have generally accepted and understood in terms of formulation science. Emulsions and microemulsions may also be employed. Emulsions, as defined herein, represent a mixture of two or more liquids that are normally immiscible; more specifically, a SFA and water. Microemulsions are clear, thermodynamically stable, isotropic liquid mixtures of a SFA and water, frequently in combination with a surfactant. For the purposes of removing ear wax from animals or humans, 1) emulsion compositions composed approximately of 40% SFA to 60% SFA and 40% to 60% water may be used; 2) particle size of at least 5 nm and less than 200 nm is preferred and the microemulsion is a liquid and composed of 20 to 95 wt-% SFA.

In this invention, compositions are suitable for administration to the ear of either a animal or human. Such compositions may be delivered to the ear canal by a mechanical spray device incorporated into the package. Compositions that are emulsions or microemulsions may also be used. Co-solvents may also be included in compositions and include glycerol, propylene glycol, polyethylene glycol, triglyceride oils, liquid mono- or diglycerides and hydrofluorocarbons. The purpose of co-solvents is to provide for lubrication of accumulated ear wax and to facilitate the removal of impacted ear wax in particular.

Compositions may also incorporate surfactants; such surfactants include polysorbates, 4-(1,1,3,3-tetramethylbutyl) phenol/poly(oxyethylene) polymers, poly(oxyethylene)-poly(oxypropylene) block copolymers, polyethylene glycol esters of fatty acids, and polyoxypropylene ethers of higher alkanes ($C_{12}$-$C_{18}$) to aid in removal of impacted ear wax.

Sodium perborate and sodium bicarbonate or sodium carbonate have been used in OTC products to aid in the removal of cerumen, and may be present in compositions. Additionally, demulcents, sometimes referred to as mucoprotective agents, may be added to the composition in small quantities to cover over irritated or inflamed skin, thereby relieving minor pain and providing fewer sites for the attachment of newly accumulated ear wax in the ear canal. Such agents include glycerin or mineral oil.

Specialized packaging to permit targeted delivery of a spray or aerosol to accumulated or impacted cerumen is a further embodiment of the present invention. Fitting the package with a mechanical cap-sprayer of a diameter from 0.2 cm to 0.4 cm and 1.9 cm to 2.4 cm and capable of being inserted into the ear canal allows for compositions to be sprayed directly onto accumulated and impacted cerumen. SFA compositions included herein are capable of solubilizing and aiding in removal of ear wax quickly. In order to help maintain the ear canal clean and relatively free of accumulated ear wax, a part of a 'maintenance program' includes the use of cotton buds that have been wetted with SFA compositions. Cotton buds are removed from unit-of-use packages and used to gently swab the ear canal, collecting recently deposited ear wax. Regular use of cotton buds wetted with composition significantly reduces occurrence of impacted cerumen.

The invention is illustrated in additional detail by the following examples.

Example 1

Aliquots of F6H8 semi-fluorinated alkane were placed into each of 6 test tubes. Ear wax was collected from animals and humans on cotton buds via gentle swabbing of the ear canal. The same approximate amount of ear wax was collected onto each cotton bud. Each cotton bud was swirled through the aliquot (approximately 1 ml) of the F6H8 SFA liquid in one test tube. In the first series of tests, the study was repeated three times for cotton buds with ear wax from dogs; in following three tests, cotton buds laden with cerumen from humans were utilized. In each case, the ear wax was dispersed within one min or less with gentle agitation. The term 'dispersed' is used here to denote that the cerumen portion of the ear wax plug was dissolved in the SFA; however, strands of hair, cellular materials and other debris remained undissolved. When these tubes of cerumen and SFA were allowed to stand for about 2 hours, the liquid separated into two distinct parts: the upper portion contained material with a fluffy appearance with a waxy consistency. Other materials remained suspended in the second, lower, phase of the tube. On microscopic examination, cellular material was present, as were hair stands and other amorphous matter. These results were unanticipated considering the label claims of other commercial ear wax treatment products such as Murine Ear Wax Removal Drops or Debrox Earwax Removal and formulations of 5% sodium bicarbonate and hydrogen peroxide (3%).

Example 2

Approximately 100 mg of human ear wax was weighed into each of four small test tubes and numbered 1-4. In a second series, approximately 100 mg of animal cerumen from dogs was placed into four different test tubes and numbered 5-8. About 1 ml of the following material was then added to the respective dishes as follows: (1) to tubes #1 and 5, F6H8; (2) to tubes #2 and 6, hydrogen peroxide, 3%; (3) to tubes #3 and 7, carbamide peroxide, 6.5% (Murine Earwax Removal Drops); and (4) to tubes #4 and 8, sodium bicarbonate, 5% (prepared by dissolved 5 grams of sodium bicarbonate in 100 ml of distilled water. Results of these studies are presented in Table 1, below.

TABLE 1

Effects of Common Remedies and SFA ($F_6H_8$) on Human and Animal (Dog) Ear Wax (Cerumen) Samples

|  | 30 Seconds | | 5 Minutes | | 15 Minutes | |
| --- | --- | --- | --- | --- | --- | --- |
|  | Human | Dog | Human | Dog | Human | Dog |
| Sodium Bicarbinate, 5% | NC | NC | NC | NC | NC | NC |
| Hydrogen Peroxide, 3% | NC | NC | BP | BP | BP, SG | BP, SG |
| Carbamide peroxide, 6.5% | NC | NC | NC | NC | NC | NC |
| SFA ($F_6H_8$) | FD | FD | FD | FD | FD | FD |

Legend:
NC, No Change
BP, Bubbles Produced
SG, Softening
FD, Fully Dispersed

Data presented in Table 1 indicates:

At 30 seconds with gentle agitation, F6H8 fully dispersed (FD) ear wax samples from both humans and dogs, whereas solutions of sodium bicarbonate 5%, hydrogen peroxide 3% or carbamide 6.5% failed to produce visible changes to ear wax samples.

At 5 minutes, bubbles were present (BP) around particles in tubes #2 and 6 containing human and dog ear wax with hydrogen peroxide 3%. The remaining tubes remained visually unchanged vs observations recorded in (1) above.

At 15 minutes, bubbles remained present (BP) around particles of cerumen samples from humans and dogs (tubes #2 and 6.) In addition, around edges of cerumen particles, some Softening (SG) of ear wax particles, as evidenced by wisps of material that were visible with gentle agitation. No other changes vs those recorded in (1) above were observed.

Example 3

Examples of certain preferred compositions are presented in Table 2, with ingredients listed by weight/volume percentages. In each column, a preferred composition of a particular type is presented.

TABLE 2

| Ingredient | A | B | C | D |
| --- | --- | --- | --- | --- |
| SFA | q.s. | q.s. | q.s. | q.s. |
| Sodium bicarbonate | — | 5 | 5 | 5 |
| Glycerin |  | 7 | 7 | 7 |
| Sodium perborate |  | 0.5 |  | 0.5 |
| Tween 20 (surfactant) |  | 0.5 |  |  |

Example 4

The effectiveness of F6H8 as a prophylaxis to prevent or retard accumulation of ear wax was evaluated in one human and one dog. The ear canal of the man and the canine were cleaned thoroughly prior to the evaluation of prophylaxis with SFA. Then, on a regular basis (five of seven days on average), 20-25 ul of F6H8 were applied to a cotton bud and the right ear only of each subjects was gently swabbed for about 15 seconds. In each instance, the contralateral ear served as a control in this study. At the end of the three month trial, the right ear of both test subjects was visibly cleaner and contained less ear wax and associated hair and other debris. Visual observation was confirmed by using a clean cotton bud to swab each ear of both subjects for 10-15 seconds. The cotton bud used to swab the right ear collected less ear wax than did the clean cotton bud used to swab the untreated left ear from both the human and the dog.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for the treatment, softening and removal of ear wax by administering to an ear canal of a subject in need thereof a composition consisting of:
   a molecule of formula:

RFRH or RFRHRF, wherein RF is a perfluorinated hydrocarbon segment with 20 or less carbon atoms, and RH is a non-fluorinated hydrocarbon segment with 3 to 20 carbon atoms, and
   at least one of a cosolvent, surfactant, sodium carbonate, sodium bicarbonate, sodium perborate, water demulcent, or preservative, wherein the ear wax is dissolved upon contact with the composition; wherein the composition is in a form of an emulsion or a microemulsion; wherein the composition is inserted in a package.

2. The method of claim 1, wherein the semifluorinated alkane is a compound of formula RFRH, wherein RF is a linear perfluorinated hydrocarbon segment with 4 to 12 carbon atoms, and wherein RH is a linear alkyl group with 4 to 8 carbon atoms.

3. The method of claim 1, wherein the semifluorinated alkane is selected from at least one of F4H5; F4H6; F4H8; F6H6; or F6H8.

4. The method of claim 1, wherein the cosolvent that is physiologically compatible, selected from glycerol, propylene glycol, polyethylene glycol, triglyceride oils, liquid mono or diglycerides and hydrofluorocarbons.

5. The method of claim 1, wherein the surfactant selected from at least one of polysorbates, 4-(1,1,3,3-tetramethylbutyl) phenol/poly(oxyethylene) polymers, poly(oxyethylene-poly(oxypropylene) block copolymers, polyethylene glycol esters of fatty acids, or polyoxypropylene ethers of higher alkanes (C12-C18).

6. The method of claim 1, wherein the demulcent is glycerin, or mineral oil, or both.

7. The method of claim 1, wherein the demulcent present in the amount of about 1 weight/volume percent to about 20 weight/volume percent.

8. The method of claim 1, wherein the preservative is selected from at least one of: benzalkonium chloride or other quarternary ammonium preservative, stabilized oxychloro complexes (Purite), sodium perborate, or mixtures thereof.

9. The method of claim 1, wherein the package is a container coated internally with materials to prevent vapor permeation of the SFA through the packaging material or the package is overwrapped with polymer to prevent escape of the SFA.

10. The container of claim 9 is a plastic container.

11. The method of claim 1, wherein the package is inserted in a package fitted with a cap-sprayer of a diameter from 0.2 cm to 0.4 cm such that it is capable of being inserted into the ear canal, and the cap-sprayer is from 1.9 cm to 2.4 cm in length.

12. The cap-sprayer of claim 11 has an extension for fitting into the ear canal.

13. The method of claim 1, wherein the subject is an animal an animal.

14. The method of claim 1, wherein the composition is an emulsion comprising about 40 wt-% semifluorinated alkane (SFA) to 60 wt-% water, to SFA and 60 wt-% to 40 wt-% water.

15. The method of claim 1, wherein the composition is an emulsion with a particle size of at least 5 nm and less than 200 nm.

16. The method of claim 1, wherein the composition is a microemulsion in a liquid composed of 20 to 95 wt-% SFA.

17. A composition for the treatment, softening and removal of ear wax by identifying a subject in need of ear wax removal and administering to an ear canal of the subject consisting of:
   a molecule of formula:

RFRH or RFRHRF, wherein RF is a perfluorinated hydrocarbon segment with 20 or less carbon atoms, and RH is a non-fluorinated hydrocarbon segment with 3 to 20 carbon atoms, and
   at least one of a cosolvent, surfactant, demulcent preservative, or water and the composition is adapted for administration to the ear canal, wherein the ear wax is dissolved upon contact with the composition wherein the composition is formulated as an emulsion or a microemulsion.

18. The composition of claim 17, wherein the semifluorinated alkane is selected from F4H5; F4H6; F4H8; F6H6 and F6H8.

19. The composition of claim 17, wherein the cosolvent is selected from the group consisting of glycerol, propylene glycol, polyethylene glycol, triglyceride oils, liquid mono or diglycerides and hydrofluorocarbons.

20. The composition of claim 17, wherein the surfactant is selected from the group consisting of polysorbates, 4-(1,1,3,3-tetramethylbutyl) phenol/poly(oxyethylene) polymers, poly(oxyethylene-poly(oxypropylene) block copolymers, polyethylene glycol esters of fatty acids, or polyoxypropylene ethers of higher alkanes ($C_{12}$-$C_{18}$).

21. The composition of claim 17, wherein the composition is an emulsion comprising about 40 wt-% semifluorinated alkane (SFA) to 60 wt-% water, to SFA and 60 wt-% to 40 wt-% water.

22. The composition of claim 21, wherein the emulsion has a particle size of at least 5 nm and less than 200 nm.

23. The composition of claim 21, wherein the emulsion is a microemulsion in a liquid composed of 20 to 95 wt-% SFA.

24. A method for the treatment, softening and removal of ear wax by administering to an ear channel of a subject in need thereof a composition consisting of: a molecule of formula: RFRH or RFRHRF,
   wherein RF is a perfluorinated hydrocarbon segment with 20 or less carbon atoms, and RH is a non-fluorinated hydrocarbon segment with 3 to 20 carbon atoms, and
   at least one of a cosolvent, surfactant, sodium carbonate, sodium bicarbonate, sodium perborate, water a bubbling agent, demulcent, or preservative, wherein the ear wax is dissolved upon contact with the composition; wherein the composition is wetted with cotton buds, wherein the cotton buds are in individually sealed unit-of-use packaging material.

25. The method of claim 24, wherein the packaging material is preventing diffusion of the composition from the package.

* * * * *